United States Patent [19]

Miyazaki et al.

[11] Patent Number: 4,576,174
[45] Date of Patent: Mar. 18, 1986

[54] MICRO ELECTRODE

[75] Inventors: Hiroshi Miyazaki; Masato Ikeda, both of Nara, Japan

[73] Assignee: Shionogi & Company, Ltd., Osaka, Japan

[21] Appl. No.: 509,034

[22] Filed: Jun. 29, 1983

[30] Foreign Application Priority Data

Jul. 8, 1982 [JP] Japan .................. 57-119035

[51] Int. Cl.<sup>4</sup> .............................................. A61B 5/04
[52] U.S. Cl. .................... 128/639; 128/642; 128/784
[58] Field of Search ............... 128/642, 639, 784, 734, 128/640-641, 643-644, 783, 793, 798, 802-803, 419 P

[56] References Cited

U.S. PATENT DOCUMENTS 4,417,581 11/1983 Dawson .................. 128/642 X
4,461,304 7/1984 Kuperstein .................. 128/642

OTHER PUBLICATIONS

Armstrong-James et al., "Carbon Fibre Microelectrodes"; J. of Neuroscience Methods, 1, No. 3; 10-1979, pp. 279-287.
Alferdinck et al.; "Two Types of Bipolar Microelectrodes for Intraretinal Use"; J. of Neuroscience Methods; 3, No. 4; 4-1981, pp. 397-404.
DeLuca et al.; "An Electrode for Recording Single Motor Unit Activity During Strong Muscle Contractions", IEEE Trans. on Biomed. Engr., vol. BME-19, No. 5, 9-1972, pp. 367-372.
Starrenburg et al.; "Carbon Fiber as an Electrode Material"; IEEE Trans. on Biomed. Engr., vol. BME-29, No. 5; 5-1982, pp. 352-355.
Analytical Chemistry, vol. 51, No. 9, pp. 1483-1486 (1979).

Primary Examiner—Lee S. Cohen
Assistant Examiner—Angela D. Sykes
Attorney, Agent, or Firm—Birch, Stewart, Kolasch & Birch

[57] ABSTRACT

An improved micro electrode and in its production method is disclosed. The electrode includes a tapering capillary tube of which the thicker end is 2 mm or smaller in the outside diameter, a conductive filament of 50 μm or smaller in the outside diameter, an outer lead wire and a filler which is packed in the cavity of the capillary tube. The improvement comprising a direct connection of the conductive filament with the outer lead wire in the cavity of the capillary tube and the use of an insulating resin as the filler. The production method comprises a step of threading the conductive filament into the tapering capillary tube to make the tip of the filament project from the needle end of the capillary tube. The method is improved by filling at least part of the cavity of the capillary tube with a volatile solvent to facilitate the threading.

1 Claim, 3 Drawing Figures

MICRO ELECTRODE

BACKGROUND AND FIELD OF THE INVENTION

The present invention relates to a micro electrode and a method for producing the same.

The micro electrode is, in general, designed to be directly inserted in a deep location in a living body. In addition to a passive function of simply picking-up a biological signal from the location, it may be used to have an active function of supplying the site of insertion with external electric energy to effect an electrochemical reaction.

Of the micro electrodes, those having such an active function are designated as "micro working electrode" and useful in analyzing minute amounts of substances produced at the location of the living body as a result of the electrochemical reaction, by means of voltammetry. The result of the measurement can be processed by an external appliance to give valuable information on bioelectrochemical phenomena of the living body.

In addition, the micro working electrode can be placed in a fluid path of liquid chromatography and used in detecting minute or trace amounts of the substance included in the flowing liquid.

DESCRIPTION OF THE PRIOR ART

Since this micro working electrode is required to be inserted in and fixed at a specified site of extremely small dimension, for instance, around the nuclei of cranial nerves of the rat, the whole structure of the electrode has to be designed to meet many restrictive conditions.

The electrode is usually structured to have core components, for example, a conductive filament and an outer lead wire, and supporting components, such as, an envelope of physiologically inert material, for instance glass, and a filler of, for a resinous material, for embedding the core components in the envelope.

The exposed segment of the conductive filament, which projects from the tip of the envelope and serves as the site of the electrochemical reaction, should be small in size in order to give the electrode a high selectivity at the location where it contacts the living body, and the filament itself should be as thin as possible. As the conductive filament, a thin metal wire has heretofore been used. However, a metal wire as thin as 100 $\mu$m has insufficient mechanical strength. In addition, some metals are inherently not suited for the defined purpose due to their electrochemical properties. Moreover, the micro working electrode is required to be constructed to retain a residual current as small as possible and therefore the insulation around the exposed segment is important.

Recently, use of carbon fiber for the purpose of the filament has been proposed, and a method of electrode construction and use have been reported (See, for instance, Jean-Luc Ponchon et. al., ANALYTICAL CHEMISTRY, 51(9), 1483–1486, 1979).

Although the carbon fiber is excellent in its mechanical properties, e.g., deflective strength, and may be finished to a very thin monofilament, it is unexpectedly difficult to handle in assembling a micro electrode. In the case where a tapering glass capillary tube is selected as a suitable envelop, the manipulation in threading a very thin carbon monofilament into the needle end of the capillary tube has actually been much more difficult than expected.

According to the method disclosed in the above cited report, a glass tube is worked by drawing using a pipet puller to obtain a tip diameter of a few $\mu$m and by cutting the tube into a capillary tube (length, 10 to 30 mm). A carbon fiber (length, 20 to 40 mm; diameter, 8 $\mu$m) is threaded into the capillary until it is blocked by the fringed tip. The glass capillary is cut at the level where the fiber is blocked, thus enabling the fiber to be pushed a few mm through the capillary. This method minimizes the interstitial space between the capillary and the carbon fiber.

The cavity of the capillary is then packed with a conductive paste (polyester resin containing graphite powder), first by inverting the capillary into a mass of the conductive paste to fill a part of the cavity with the paste and then by forcing the filled paste into the tip of the capillary tube.

At the tip of the capillary, the resin is separated from the graphite powder (about 1 $\mu$m in diameter) to ensure insulation from the electrode's inactive part. Connection of the carbon fiber with an external lead wire is made simply by pushing it as far as possible into the barrel filled with the paste, in other words, the carbon monofilament is connected with the outer lead wire as a result of being embedded in a common conductive resin.

As will be described later with the description of the preferred embodiment, the electrode prepared in such a way is not satisfactory in its performance and in yield of its production.

SUMMARY OF THE INVENTION

Diversified investigation has been conducted in order to develop a simple and reliable structure of a micro working electrode which will overcome disadvantages of the abovementioned method and a method suited for mass-producing the same in an easy and simple operation of high productivity. As a result, in accordance with the present invention, it has been determined that the threading step of the carbon fiber into the capillary tube can be made easier by filling the cavity of the capillary tube with a volatile solvent, whereby a direct connection of the carbon monofilament with the outer lead wire is also made possible prior to the threading step. The present invention is based on these findings.

Namely, according to the present invention there is provided an improved micro electrode consisting of a tapering capillary tube of which the thicker end is 2 mm or smaller in the outside diameter, a conductive filament of 50 $\mu$m or smaller in the outside diameter, an outer lead wire and a filler which is packed in the cavity of the capillary tube, characterized in that the conductive filament is directly connected with the outer lead wire in the cavity of the capillary tube and the filler is an insulating resin.

According to another aspect of the present invention there is provided an improvement in the method for producing a micro electrode which comprises a step of threading a conductive filament into a tapering glass capillary tube to make the tip of the filament project from the needle end thereof, characterized in that at least part of the cavity of the capillary tube is filled with a volatile solvent during the threading step.

DESCRIPTION OF THE PREFERRED EMBODIMENT

The conductive filament, referred to above, is preferably carbon fiber and a single monofilament is usually used, though two or more monofilaments may be used in bundle form to enlarge the effective surface area of the electrode and to improve the sensitivity.

A metal wire may also be used as the conductive filament and can easily be connected with the lead wire by any means, for instance, soldering. The metal wire should, however, have a deflective strength equivalent to or higher than that of the carbon fiber of the same diameter.

The conductive filament, such as a carbon monofilament or a bundle of monofilaments, is preferably connected directly with the outer lead wire by, for instance, gluing the former on the latter with a conductive resin containing carbon powder (usually available as a conductive paint or adhesive) prior to the threading step. The employment of the method of the present invention has solely made such direct connection and the structure incorporating the connected body possible.

Since the conductive filament is directly connected with the outer lead wire and the conductive segment in the cavity of the capillary tube is strictly limited to the zone where they both are connected, the remaining part of the cavity needs not be conductive and is usually filled with an insulating resin in the electrode structure of the present invention. This structure ensures the highly reliable connection and a high degree of insulation as compared with the conventional structure.

In addition, since the size of a pinhole formed at the needle end of the capillary tube may be widely varied (about 7–100 $\mu$m), the productivity in terms of yield is sufficiently high. The volatile solvent used in the above-mentioned production process can be selected from alcohols, such as ethanol and methanol, ketones, such as acetone and methyl ethyl ketone, ethers, such as diethyl ether and tetrahydrofran, esters, such as ethyl acetate, and hydrocarbons, such as benzene and hexane. Water can also be used as the volatile solvent in certain cases; alcohols, particularly ethanol is preferred in view of the ease and safety in operation and the required short drying time.

Since the capacity of the capillary is very small, its entire space is usually filled with this volatile solvent, but only a part, which corresponds to the needle end of the cavity, is desired to be moistened.

BRIEF DESCRIPTION OF THE DRAWINGS

The present invention will now be described in more detail by referring to the attached drawings, in which.

DETAILED DESCRIPTION

Figure 1:
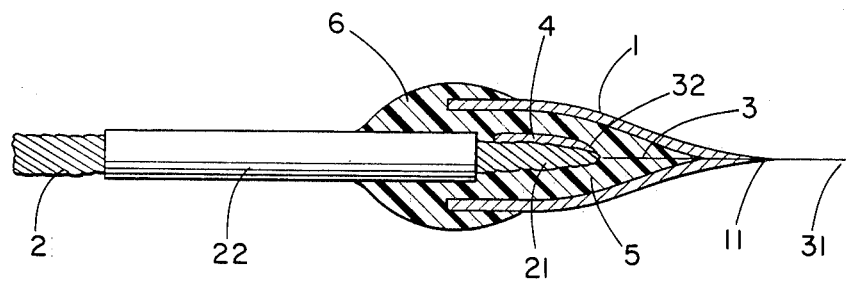
FIG. 1 is a partly cut-out side view of a micro electrode embodying the present invention.

In the drawings, there is provided a capillary tube 1, an outer lead wire 2 with an insulator coating layer 22, a carbon fiber 3, a carbon powder-containing conductive resin layer 4, an insulator resin layer 5 and a protective resin layer 6.

The tip 31 (length, 0.1 to 0.5 mm) of the carbon monofilament 3 projects from the needle end 11 of the capillary tube 1 to be exposed. The root segment of the carbon monofilament 3 is glued on a connecting segment 21 of the outer lead wire 2, where its insulator coating layer 22 is removed, by the carbon powder-containing conductive resin layer 4.

The opposite end of the lead wire 2 is exposed from the thicker end of the capillary tube for being connected with outside appliances.

In producing such an electrode, the carbon monofilament 3 is first glued on the outer lead wire 2 to give a combined body.

Separate from this, the tapering capillary tube 1 is prepared by working a micropipette (about 100 $\mu$L in capacity, 1.5 mm in outside diameter and 1.1 mm in inside diameter) by a pipet puller to form a needle end (about 8 $\mu$m to 200 $\mu$m in the inside diameter) and by cutting the micropipette at the pulled portion to give pieces of about 15 mm in length.

Figure 2:
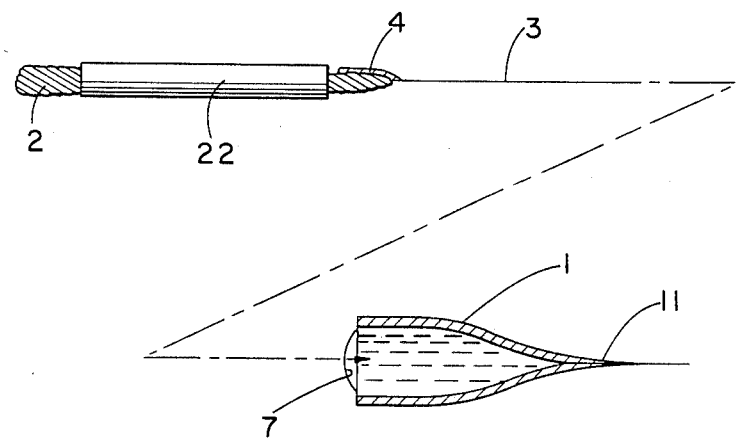
FIGS. 2 and 3 are similar schematic views showing the production process thereof.

The cavity of the capillary tube 1 is filled with a volatile solvent 7 (ethanol, about 10 $\mu$L), into which the combined body is introduced, as indicated by the chained line (FIG. 2), so that the tip 31 of the carbon monofilament 3 is threaded into the needle end to project therefrom. If the solvent is not used and the cavity is left empty, the introduction and threading of the carbon monofilament 3 is very difficult resulting in frequent breakage and sometimes the manipulation itself is substantially impossible.

Figure 3:
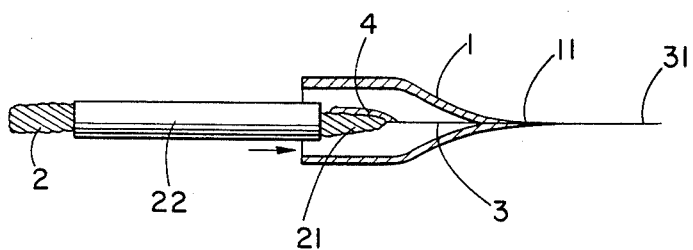

After completion of the threading step, the glued segments of the carbon monofilament 3 and the lead wire 2 are enclosed in the cavity of the capillary tube 1 (FIG. 3).

After the volatile solvent is completely removed from the cavity generally within a short drying time, an insulating resin 5, in its fluid state, is introduced into the cavity of the glass capillary tube 1 from its thicker end by a syringe along the direction indicated by an arrow (FIG. 3) to embed the combined body.

The fluid resin is evenly distributed up to the tip of the needle end 11 of the capillary tube 1 through capillary action yet it will not leak from the interstice between the monofilament 3 and the encircling glass part. The resin is preferably of low viscosity in its fluidity in order to exhibit the best possible capillary action.

Thereafter, the thicker end of the capillary tube 1 is protected with another insulator resin layer 6. As the resin, that used in embedding the combined body can be used, though it is preferred to select one providing a more complete protection function and having a shorter hardening time.

In the illustrated example, TORAYCA T 300 or M 40, available from Toray Corporation, is used as the carbon fiber, Dotite SH-3A (Epoxide resin base), available from Fujikura Kasei K. K., is used as the conductive resin, Araldide AY 103/HY 956, available from Ciba-Geigy, is used as the resin for embedding and Hi-Super, available from Cemedain K. K., is used as the protective coating layer.

The thus obtained micro electrode is finished by cutting the tip 31 of the carbon monofilament 3 by 500 $\mu$m, and subjecting it to a conduction test and an electrolytic treatment which is a cyclic anodic pre-treatment in dilute sulfuric acid.

Electric resistance of the electrode is around 4–5 KOhms mainly attributable to that of the carbon monofilament. Residual current is in the order of nA (nano ampere).

In a comparative experiment, an electrode of the same structure as that of the illustrated example is prepared by substituting Dotite SH-3A for Araldide AY 103/HY 956 as a resin for embedding the combined body (solvent excessively contained in Dotite SH-3A had been extracted therefrom before use).

The obtained electrode showed a very large value of the residual current (about 100 times of the illustrated example) and cannot be used in a precision measurement.

Incidentally, since the electric resistance of the electrode is mainly accountable for that of the carbon monofilament, the use of a plurality of the monofilaments in a bundle will decrease the electric resistance. This facilitates the adjustment of the electrode to a measuring appliance.

On the other hand, the electrode may be finished by cutting the tip of the monofilament up to 100 $\mu$m or shorter in order to improve the selectivity of the spot on location where it is dibbled. In an extreme case, the electrode may be in the form of a disk in a sense of electrical equivalence.

What is claimed is:

1. A micro electrode consisting of a tapered glass capillary tube forming a cavity, said tube having a thick end with an outside diameter of 2 mm or smaller and a needle end, an outer lead wire within said tube and extending from said thick end thereof, a carbon fiber conductive filament having an outside diameter of 50 $\mu$m or smaller and having a first end and a second end, a conductive resin containing carbon powder within said cavity of said capillary tube connecting said outer lead wire to said first end of said conductive filament, a second end of said conductive filament projecting from said needle end of said capillary tube, an insulative resin filler packed in said cavity of said capillary tube around said outer lead wire where said wire is connected to said conductive filament, and a protective resin at said thick end of said capillary tube formed about said lead wire and said tube.

* * * * *